United States Patent [19]

Frimberger

[11] Patent Number: 4,846,175

[45] Date of Patent: Jul. 11, 1989

[54] PROBE FOR INTRODUCTION INTO THE HUMAN OR ANIMAL BODY, IN PARTICULAR A PAPILLOTOME

[75] Inventor: Eckart Frimberger, Munich, Fed. Rep. of Germany

[73] Assignee: Erintrud Frimberger, Kempten, Fed. Rep. of Germany

[21] Appl. No.: 133,955

[22] Filed: Dec. 17, 1987

[30] Foreign Application Priority Data

Dec. 18, 1986 [DE] Fed. Rep. of Germany ....... 3643362

[51] Int. Cl.⁴ .............................................. A61B 17/36
[52] U.S. Cl. ................................................ 128/303.15
[58] Field of Search .... 128/1.6, 303.1, 303.13–303.17; 604/164, 170, 282

[56] References Cited

U.S. PATENT DOCUMENTS

| | | | |
|---|---|---|---|
| 3,906,938 | 9/1975 | Fleishhacker | 604/170 |
| 4,315,509 | 2/1982 | Smit | 128/1.4 |
| 4,325,374 | 4/1982 | Komiya | 128/303.15 |
| 4,485,812 | 12/1984 | Harada et al. | 128/303.15 |
| 4,724,836 | 2/1988 | Okada | 128/303.15 |

FOREIGN PATENT DOCUMENTS

| | | | |
|---|---|---|---|
| 524909 | 5/1956 | Canada | 138/56 |
| 2426781 | 12/1975 | Fed. Rep. of Germany | 128/303.15 |
| 2657256 | 6/1978 | Fed. Rep. of Germany | 128/303.15 |
| 3347122 | 6/1985 | Fed. Rep. of Germany | 128/303.14 |

OTHER PUBLICATIONS

Endoscopic Papillotomy, Joseph E. Geenen and Edward T. Stewart, Chapter 12, pp. 334–341.

Primary Examiner—Max Hindenburg
Attorney, Agent, or Firm—Scully, Scott, Murphy & Presser

[57] ABSTRACT

A probe for introduction into the human or animal body, having a sheath of flexible material and a traction element extending longitudinally in the sheath that is fastened to the sheath for the purpose of effecting curvature by exerting traction at its outer end and runs on one side of the sheath in the region of curvature (B), in particular a papillotome, is to be designed so as to obtain a specified direction of curvature. For this purpose the sheath has different moments of resistance to bending in two mutually perpendicular directions across its cross-section, and the traction element is arranged on the side towards which the sheath has the smaller moment of resistance.

10 Claims, 2 Drawing Sheets

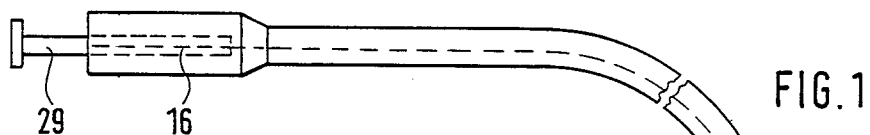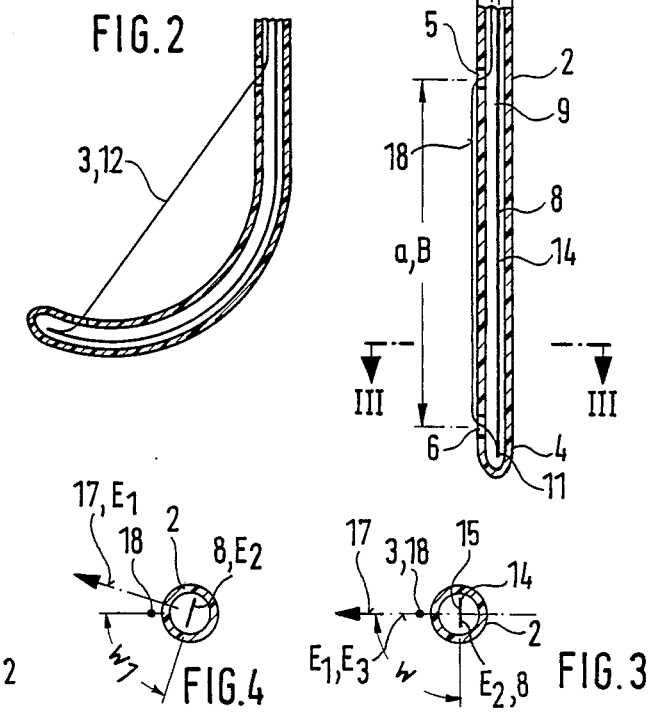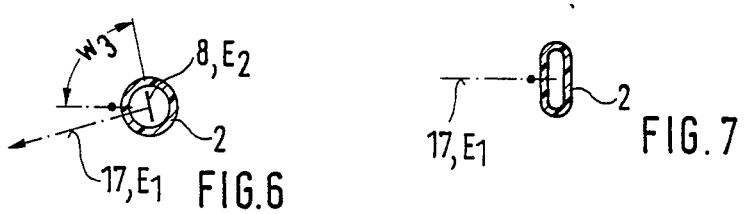

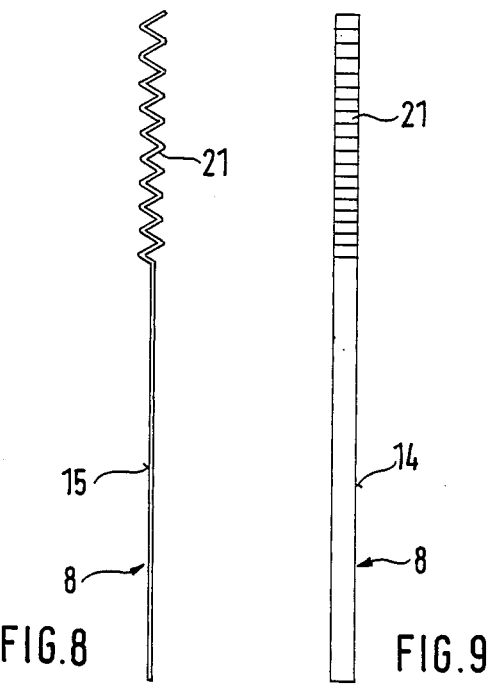
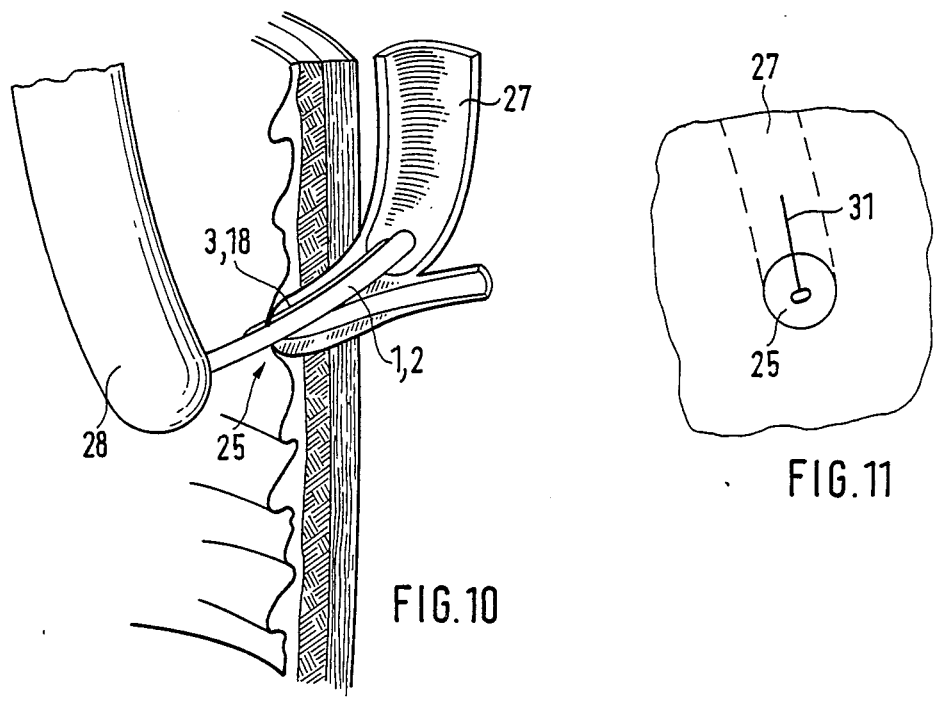

PROBE FOR INTRODUCTION INTO THE HUMAN OR ANIMAL BODY, IN PARTICULAR A PAPILLOTOME

BACKGROUND OF THE INVENTION AND PRIOR ART

The least complicated method for the removal of stones from the bile duct at present consists of the endoscopic splitting of the papilla and subsequent extraction of the stone.

For this purpose a perorally introduced lateral-viewing duodenoscope is used, after passage through the esophagus and the stomach, to locate the discharge branch of the duodenum, where the bile duct and the pancreatic duct have a common opening in a wart-shaped protrusion (papilla).

The opening of the papilla is first intubated with a probe pushed laterally out of the duodenoscope. by means of a contrast medium injected with the probe the two ducts are made visible radiologically, when the stones show up as spaces in the contrast medium. After the stones have been revealed in this way the probe is removed and in its place a so-called papillotome is introduced into the bile duct—likewise through the duodenoscope—so that the section of the papillotome that can be curved by means of the traction wire is in the region of the papilla. By traction on the traction wire at its outer end, whereby the papillotome is caused to curve and the traction wire is stretched as a chord, and by simultaneously connecting the traction wire to a source of current, the papilla is cut in conformity with the upwardly extending bile duct. The stone can then spontaneously emerge through the widened papilla, or be withdrawn with an instrument (a collecting basket).

Because of physical conditions the chord of an arc formed by the traction wire after the traction always faces upward, i.e. approximately along the line of the duodenoscope. The direction of the cut is thus substantially predetermined, and in practice it is not possible, if so desired, to make a lateral cut without changing the position of the duodenoscope, which would require the duodenoscope to be re-oriented. This state of affairs is of considerable importance, since the cut in the papilla must always correspond to the course of the upwardly extending bile duct or of the bulge adjoining the papilla. A cut laterally across this bulge would be a serious complication because of perforation, with possibly fatal results.

With this known design both the introduction of the probe described above and the cutting open of the papilla by means of the papillotome corresponding to the upward course of the bile duct are difficult, since the direction of curvature of the probe or of the papillotome depends solely on the force of traction, but is not fixed, so that substantial deviations can occur.

OBJECT OF THE INVENTION

The object of the invention is to design a probe of the above mentioned kind so that a specified direction of curvature can be obtained.

BRIEF DESCRIPTION OF THE INVENTION

In the design according to the invention the direction of curvature is predetermined by the direction in which the smaller resistance moment of the sheath acts, and is thus stabilized. This applies both to the case in which the smaller resistance moment acts in the same direction as that in which the tractive force acts and also to the case in which the direction of the smaller resistance moment differs from the direction of the tractive force. In the latter case a desired direction of curvature can be achieved by selecting a particular direction of the smaller resistance moment, which also makes it possible to adapt to the anatomical conditions as well as giving the desired stabilization.

The different resistance moments in mutually perpendicular directions across the cross-section of the sheath can be achieved both by an elongated crosssection of the sheath section and by additional elements attached to the sheath that have the abovementioned relative resistance moments. For this purpose a bending element in the form of a leaf spring, of which the direction of bending or curvature is determined by the different ratios of breadth and thickness, is particularly suitable. Such an additional element can be attached to the sheath in a simple manner, e.g. by accommodating it in the space inside the sheath, by embedding it in the wall of the sheath or even by arranging it on the outside of the sheath.

It is also an important advantage to make available to the surgeon performing the operation a set of assorted probes according to the invention in which the direction of curvature or bending predetermined by the design according to the invention differs from one probe to another, for example in 10° to 15° steps. In this case the doctor carrying out the treatment can select an appropriate probe in the light of his knowledge of the anatomical conditions. A particular direction of bending or curvature or direction of cut can thus be prescribed and maintained in a simple manner.

It is also possible, within the scope of the invention, to twist the section of the sheath or the bending element to match the anatomical conditions or the desired bending or curvature, whereby it is likewise possible to obtain a match to predetermined or intended conditions.

BRIEF DESCRIPTION OF THE DRAWINGS

The invention will now be explained in more detail with reference to exemplary embodiments shown in simplified drawings, in which:

FIG. 1 shows in side view, and partially in section, a probe designed according to the invention in the form of a papillotome;

FIG. 2 shows the inner end of the papillotome in the curved condition;

FIG. 3 is a section on III—III in FIG. 1;

FIGS. 4 to 7 are sections through other designs corresponding to FIG. 3;

FIG. 8 is a side view of bending element for the papillotome;

FIG. 9 is a front view of the bending element;

FIG. 10 is a section through a duodenum showing the function of the papillotome; and FIG. 11 is a view of the papilla of the duodenum.

DETAILED DESCRIPTION OF PREFERRED EMBODIMENTS OF THE INVENTION

The papillotome indicated generally by 1 in FIG. 1 consists of a sheath 2 in which runs a traction element, preferably in the form of a wire 3, that is fixed to the papillotome 1 in the region of its introduction end, i.e. in the region of the inner end of the sheath 2. The sheath 2 consists of an elastically flexible tube, preferably of plastics material. In the region of the inner end indicated by 4 the sheath 2 has two holes 5, 6 on an axial line at a distance a from one another, the inner one, i.e. the hole 6 nearest to the inner end 4, is only a short distance from the inner end 4. The distance a amounts to about 2.5 cm.

The wire 3 is led out through the outer hole 5 so that it runs on the outside of the sheath 2 and is led back in again through the inner hole 6. The fastening of the wire 3 to the sheath 2 is done by fastening the wire 3 to a bending element in the form of a leaf spring 8, arranged in the cavity 9 of the sheath 2, to the inner end 11 of which the wire 3 is fixed. The length L of the leaf spring 8 is greater than the length of the bending section, indicated by B, in the region of which, when traction is exerted on the wire 3 at its outer end, the inner end 4 of the sheath 2 takes up the curvature shown in FIG. 2, in which the wire 3 forms a chord 12 to the arc of curvature. By means of the chord 12 it is possible in a known manner to make cuts in the tissue of the human or animal body after connecting an electric current.

In FIG. 1 the narrow side 14 of the leaf spring 8 can be seen, i.e. it is turned with one of its broad sides towards the section 18 of the wire that runs on one side relative to the sheath 2. On exerting tractive force on the wire 3 at its outer end 16 the leaf spring 8 bends in the bending plane indicated in FIG. 3 by $E_1$, as shown in FIG. 2. This bending plane $E_1$ is at right angles to the plane $E_2$ of the leaf spring 8.

Because of its narrow section, the moment of resistance to bending of the leaf spring 8 in the bending plane $E_1$ is relatively small while its moment of resistance in its own plane $E_2$ is relatively large. The leaf spring 8 thus provides guidance for the bending movement, whereby the bending movement is appreciably stabilized. This also applies to the bending back of the curved section of the sheath 2. Because of the presence of the leaf spring 8 it is not necessary to use an elastic material for the sheath 2, since this is bent back by the leaf spring 8.

In the embodiment just described the bending direction, indicated by 17, of the leaf spring 8 is the same as the direction in which the bending section B of the sheath 2 is bent, because of the one-sided arrangement of the wire 3, when traction is applied to the latter. It is however possible, and also advantageous, for reasons that will now be described, to arrange the leaf spring 8 according to FIGS. 4 to 6 obliquely to the plane $E_3$ which intersects the section 18 of wire that runs outside the sheath 2 and the central axis of the sheath 2, whereby the acute angles $w_1$, $w_2$, $w_3$ between the plane $E_3$ and the bending plane $E_1$ of the leaf spring 8 can lie to the right or the left of the wire section 18. It is preferable to provide the surgeon performing the operation with a set of several papillotomes 1, including at least one papillotome according to FIGS. 1 and 3 and at least one or two papillotomes 1, in which the leaf spring 8 is inclined at least to one side of the wire section 18 (FIGS. 4 to 6). It is further advantageous to include in the set papillotomes 1 with angles $w_1$, $w_2$ of differing magnitudes so that the surgeon can determine the direction of cut as he desires so that it substantially corresponds to the direction of bending 17 of the leaf spring 8. The difference in angle from step to step preferably amounts to 10° to 15°.

The modification according to FIG. 7 shows a tubular sheath 2 that is stabilized to in respect of its direction of bending 17 not by an additional bending element but because of the shape of its cross-section, an elongated, flattened cross-section. The direction of bending 17 is determined in this example by the direction in which the bending section B of the sheath 2 has its smaller resistance moment predetermined by the elongated cross-section. Here the direction of bending 17 matches the plane $E_1$, i.e. the bending section B is stabilized in the plane $E_1$, which is also the traction plane.

According to FIGS. 8 and 9 an extension 21 of the leaf spring 8 extends beyond the outer hole 5 in the sheath 2 for stabilization of the sheath 2 in this region. The extension 21 has a zig-zag or corrugated shape, so that the cross-sectional area required by the extension section 21 corresponds to the cross-section of the cavity 9. This contributes both to the stabilization of the sheath 2 in this region and to a sheath 2, and does not interfere with the lateral emergence from a duodenoscope which will be described later.

The papillotome 1 serves to widen the papilla indicated in FIG. 10 by 25 by means of an upwardly directed cut, so that stones (not shown) present in the bile duct 27 can be removed. The papillotome 1 is introduced by means of a lateral viewing duodenoscope 28 into the papilla 25 or into the bile duct 27, as described above. Tension is then applied by traction on the traction member that is indicated by FIG. 1 by 29 and is fastened to the wire 3, whereby the bending section B is curved (FIG. 2), and by simultaneously connecting the wire 3 to a source of current the cut indicated by 31 by in FIG. 11 is made.

It can clearly be seen in FIG. 11 that the cut 31 must be made upwards and along the bile duct 27, since otherwise it leads to perforation of the bile duct, with serious consequences.

With the design according to the invention the direction of cut, that as a result of the exertion of traction on the bending section B automatically runs substantially longitudinally of the duodenoscope 28, can be both stabilized and corrected by the leaf spring 8 or the particular cross-sectional ratio of the sheath 2.

Because of differing anatomical conditions it is often necessary to make an inclined cut 31 of which the inclination differs from the line of the duodenoscope 28. In such cases it is advantageous to have available papillotomes 1 having different angles $w_1$ to $w_3$, in order to make a cut that is adapted to the anatomical proportions. In practice the cut 31 is begun with a conventional papillotome or a papillotome 1 according to FIGS. 3 or 7. If the resulting direction of cut appears not to be optimal, which can be observed in known manner through the duodenoscope 28 or by means of radiology, the papillotome is exchanged for a papillotome with a suitable cutting angle $w_1$ to $w_3$. The alignment of the intended cutting movement can then be made without having to reposition the duodenoscope 28.

Within the scope of the invention it is possible to use other cross-sectional shapes of the sheath 2 and other bending elements or other arrangements of a bending element. It is for example possible to form the sheath, at least in its bending region B, from solid material. Instead of a leaf spring inserted in the hollow interior in the sheath 2 a leaf spring embedded in the material of the sheath or stuck onto the sheath can be used. It is also possible to form the bending region B solely from a leaf spring or a corresponding bending element.

What is claimed is:

1. A probe for introduction into the human or animal body, in particular a papillotome comprising a sheath of flexible material and a traction element extending longitudinally in the sheath, said traction element being fastened to the sheath for purpose of effecting curvature of the sheath by exerting traction at an outer end of said sheath, said traction element running on one side of the sheath in the region of curvature, wherein the sheath is tubular and flattened in the region of curvature to have an elongated oval or rectangular cross section, and wherein said sheath further has different moments of resistance to bending in two mutually perpendicular directions across said cross section, such that the traction element is arranged on the side towards which the sheath has the smaller moment of resistance to bending.

2. A probe according to claim 1, wherein the sheath has associated with it a bending element that has different resistance moments in respect of two mutually perpendicular directions across its cross-section and is so arranged that the traction element is arranged on the side towards which the bending element exhibits the smaller resistance moment.

3. A probe according to claim 2, wherein the bending element is a leaf spring.

4. A probe according to claim 2, wherein the bending element is arranged in the sheath.

5. A probe according to claim 2, wherein the traction element is fastened at the inner end of the bending element.

6. A probe according to claim 2, wherein an extension on the outer end of the bending element expends beyond the bending section.

7. A probe according to claim 6, wherein the extension has a corrugated or zig-zag shape traverse to the plane of the leaf spring.

8. A probe according to claim 1, wherein the bending plane extends on one or the other side of the traction element.

9. A probe according to claim 1, wherein said probe is provided with a traction element lying in a bending plane located between planes defined by said two mutually perpendicular directions across said cross section of said sheath, such that the cutting angle is offset from one side of the sheath having a smaller moment of resistance.

10. A probe according to claim 1, wherein said sheath has a smaller moment of resistance to bending in a direction defined by the minor axis of said oval cross section.

* * * * *